United States Patent [19]

Gibbs, Jr. et al.

[11] Patent Number: 5,685,876
[45] Date of Patent: Nov. 11, 1997

[54] DEVICE FOR RADIATION THERAPY OF RECTAL CANCER

[75] Inventors: Frederic A. Gibbs, Jr., Salt Lake City; Christopher F. Johnson, Bountiful, both of Utah

[73] Assignee: University of Utah Research Foundation, Salt Lake City, Utah

[21] Appl. No.: 529,332

[22] Filed: Sep. 18, 1995

[51] Int. Cl.$^6$ ................................................ A61B 17/00
[52] U.S. Cl. ........................... 606/1; 606/197; 128/898
[58] Field of Search .................. 606/1, 197; 128/653.1, 128/654, 898, 659

Primary Examiner—Angela D. Sykes
Assistant Examiner—Ryan Carter
Attorney, Agent, or Firm—Terry M. Crellin

[57] ABSTRACT

A device for pushing a scar in the perineal region of a patient so that the scar can be optimally positioned during radiation treatment of the rectal area of the patient. A base is positioned beneath a patient's legs as the patient lies on a radiation therapy support platform. A guide and support member extends upwardly from the base so that the guide and support member is positioned between the thighs of the patient. A slide member is supported by the guide and support member, with the slide member being constrained to slide back and forth along the guide and support member in a direction substantially parallel to the patient's legs so that pressure can be exerted on the patient's perineum by the leading end of the slide member. The slide member can be moved manually, and a retaining mechanism is provided for releasably locking the slide member in any selected position along its movement. The device is used by manually moving the slide member toward the patient's perineum so that the leading end of the slide member pushes the perineal scar cephalad and then holds the scar in proper position during subsequent radiation therapy of the rectal area of the patient.

12 Claims, 3 Drawing Sheets

DEVICE FOR RADIATION THERAPY OF RECTAL CANCER

BACKGROUND OF THE INVENTION

1. Field of the Invention

The present invention relates generally to devices used in the treatment of patients with radiation after they have undergone rectal surgery with colostomy. More particularly the invention relates to a device for pushing a scar in the perineal region of a patient who has previously had surgical removal of the rectum and anus so that the scar can be optimally positioned during radiation treatment of the rectal area of the patient.

2. State of the Art

Patients who have undergone rectal surgery with colostomy must often further undergo radiation treatment following the surgery. During the radiation treatment, the perineal scar from the previous surgery must be included in the radiation treatment. Heretofore, doctors have simply made the radiation field of sufficient size to ensure that the scar is treated. However, by making the radiation field of a sufficient size to ensure treatment of the scar, the field is of sufficient size to also produce unnecessary irradiation of the genitalia of the patient. Heretofore, there has been no effort to reduce the size of the radiation field so as to avoid unnecessary irradiation of the patient. Nor, of course, has there been any suggestion in the prior art of a simple device that can be used to push against and position the scar so that the field of radiation can be reduced to avoid the unnecessary irradiation of the genitalia of the patient.

OBJECTIVE AND BRIEF DESCRIPTION OF THE INVENTION

The principal objective of the present invention is to provide a simple mechanical device and a method of using the device to push the scar in the perineal region of a patient who has previously had surgical removal of the rectum and anus so that the scar can be optimally positioned during radiation treatment of the rectal area of the patient. A particular objective of the present invention is to provide such a device which can be used to readily and effectively push the perineal scar cephalad and hold the scar in proper position relative to the patient's radiation therapy fields which are typically directed perpendicular to the patient's body axis.

The present invention comprises a simple mechanical device for pushing a scar in the perineal region of a patient so that the scar is positioned for proper radiation therapy. By such optimal positioning of the scar, the overall size of the radiation field can be reduced and thus avoid unnecessary irradiation of the patient's genitalia.

The device of the present invention comprises a base that is positioned between the legs of a patient as the patient lies supine or prone on a radiation therapy support platform. A guide and support member extends upwardly from the base between the thighs of the patient. A slide member is supported by the guide and support member so that it can slide back and forth along the guide and support member in a direction substantially parallel to the patient's legs. The leading end of the slide member is adapted to exert an adjustable pressure on the patient's perineum to push the scar in the perineal region of the patient cephalad. A releasable locking mechanism locks the slide member in any selected position along the movement of the slide member so that when the scar is pushed to its optimum position, the slide member can be locked to hold and sustain the scar in its optimum position during subsequent radiation treatment of the rectal area of the patient. In its optimum position, the scar is subjected to the radiation as desired during the radiation treatment, but the radiation field can be reduced in size as compared to the size of the radiation field necessary to encompass the scar if the scar is not pushed cephalad to its optimum position. By reducing the size of the radiation field, the radiation dose to the skin near the scar can be reduced, and undesirable irradiation of the genitalia of the patient can be avoided.

Additional objects and features of the invention will become apparent from the following detailed description, taken together with the accompanying drawings.

THE DRAWINGS

A preferred embodiment of the present invention representing the best mode presently contemplated of carrying out the invention is illustrated in the accompanying drawings in which.

DETAILED DESCRIPTION OF THE ILLUSTRATED EMBODIMENT

Figure 1:
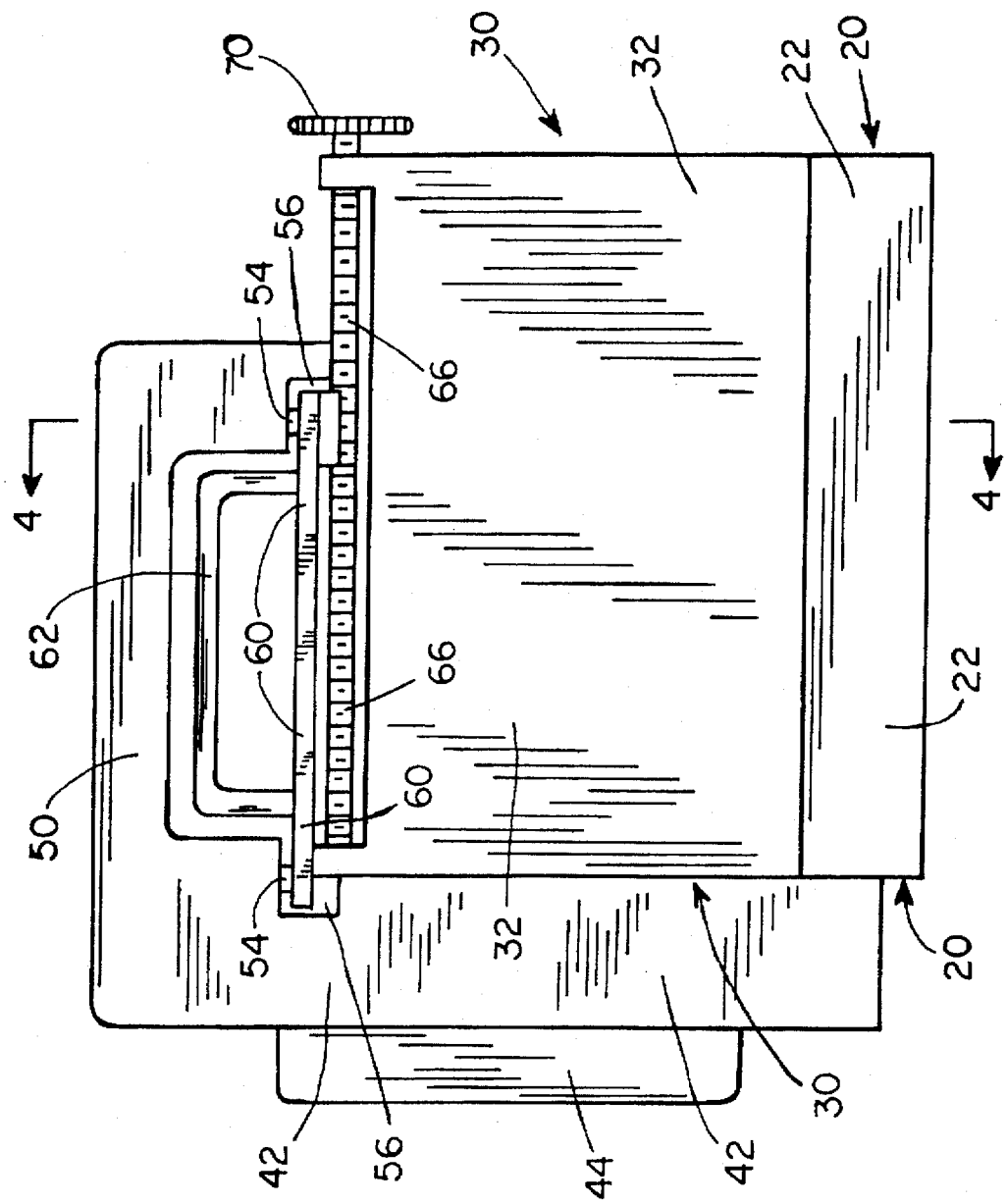
FIG. 1 is a side elevation of the device of the present invention.
Figure 2:
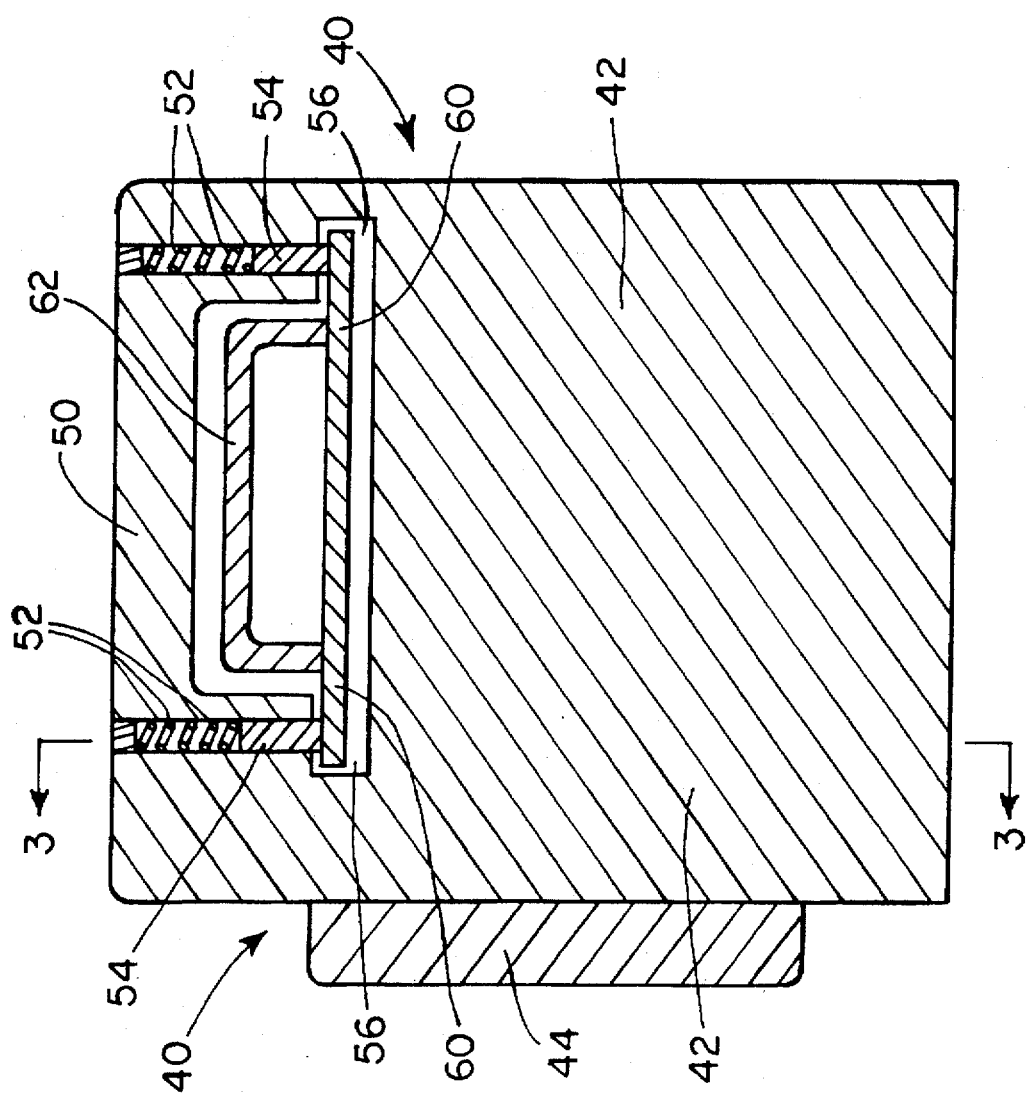
FIG. 2 is a vertical cross section of the slide member isolated from the housing, with said cross section being taken along the longitudinal axis of the slide member.
Figure 3:
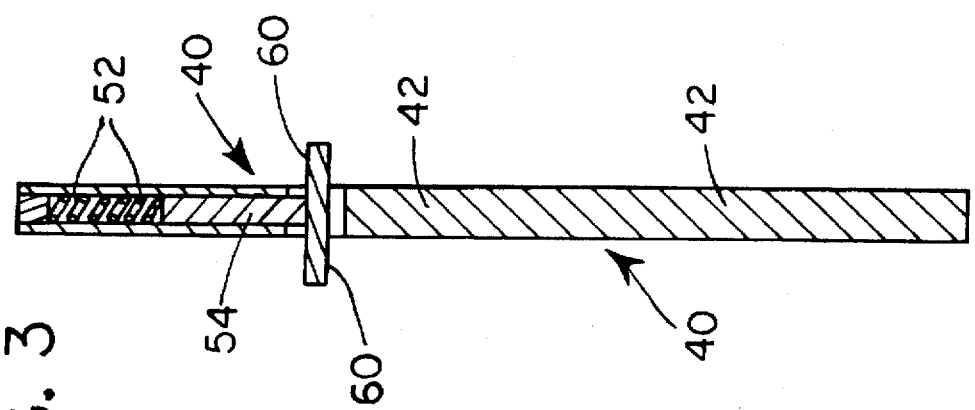
FIG. 3 is a transverse, vertical cross section through the slide member taken along line 3—3 of FIG. 2.
Figure 4:
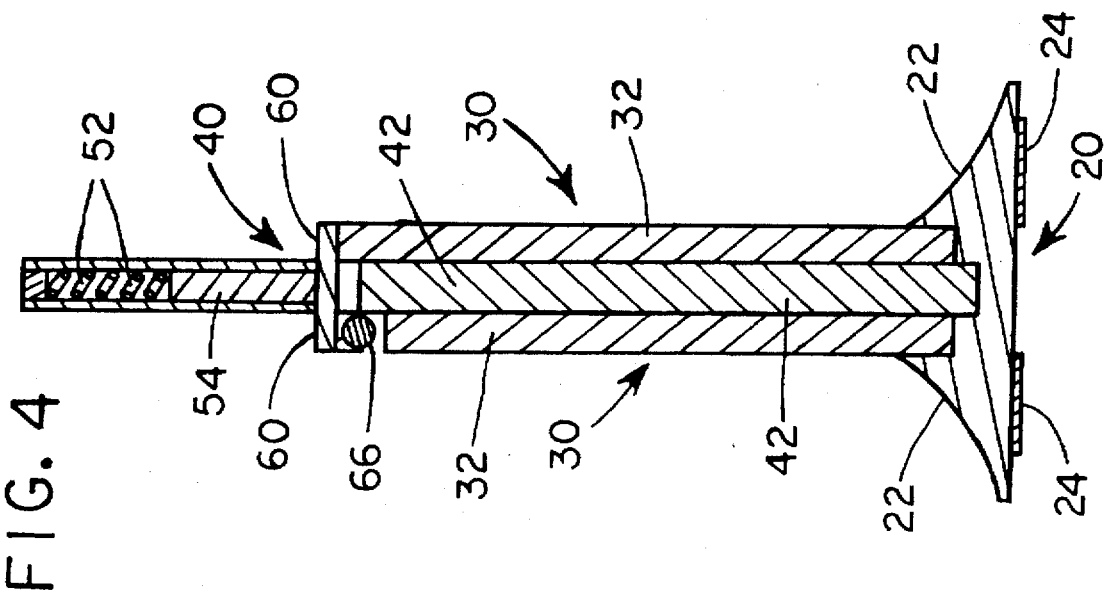
FIG. 4 is transverse, vertical cross section through the device of FIG. 1 taken along line 4—4 of FIG. 1.

In accordance with the present invention, a simple, mechanical device is provided which can be used to push a scar in the perineal region of a patient who has previously had surgical removal of the rectum and anus so that the scar can be optimally positioned during radiation treatment of the rectal area of the patient. One preferred embodiment of the device of the present invention is illustrated in the drawings.

As illustrated, the device comprises a base 20 that is adapted to be positioned beneath a patient's legs as the patient lies supine or prone on a radiation therapy support platform. The patient and platform are not shown in the drawings. The base 20 is an elongate member that is adapted to be positioned between the legs of the patient so that a longitudinal axis of the base 20 lies substantially parallel with and between the patient's legs. The base 20 has a substantially flat bottom that is adapted to lie flatwise on a sheet or other cover for the support platform. The support platform and its cover are not shown in the drawings.

The base 20 advantageously has two opposite longitudinal top sides 22 that slope inwardly from respective longitudinal side edges of the flat bottom of the base 20 toward a central, vertical plane through the longitudinal axis of the base 20 to form shallow, inwardly slanted top surfaces upon which the patient's legs rest when the patient lies on the support platform. The weight of the patient's legs then acts on the top sides 22 of the base 20 to hold the base 20 in a firm, stable position on the support platform.

The base 20 further advantageously has at least one unidirectional oriented fiber strip 24 attached to its bottom surface. The fiber strip 24 interdigitates with the weave of a sheet or cover on the support platform, and the interdigitation prevents slippage of the base 20 toward the patient's feet but permits the base 20 to be slid over the sheet or cover toward the patient's head.

A guide and support member 30 extends upwardly from the base 20 so that the guide and support member 30 is adapted to be positioned between the thighs of a patient who is lying on a radiation support platform. The guide and support member 30 comprises a pair of spaced apart, substantially planar side plates 32 that extend substantially vertically upwardly from the base 20.

A slide member 40 is supported by the guide and support member 30, with the slide member 40 being constrained to slide back and forth along the guide and support member 30 in a direction substantially parallel to the patient's legs when the device is positioned between the legs of a patient who is lying on a radiation support platform. When so positioned between the legs of a patient, pressure can be exerted on the patient's perineum by way of the leading end of the slide member 40, and the degree of pressure can be adjusted by sliding the slide member 40.

The slide member 40 comprises a substantially planar slide plate 42 that is received substantially vertically between the pair of side plates 32 that extend upwardly from the base 20. The lower edge of the slide plate 42 rests on the base 20 so as to slide back and forth along the base 20, while opposite, broad sides of the slide plate 42 are supported by the side plates 32. The opposite, broad sides of the slide plate 42 are guided in back and forth movement between and along the side plates 32.

A handle 50 is provided on the slide member 40 for manually moving the slide member 40 in its movement relative to the base 20 and the guide and support member 30. A releasable locking mechanism is associated with the slide member 40 to releasably lock the slide member 40 in any selected position along the movement of the slide member 40 relative to the base 20 and the guide and support member 30.

In use, the device of the present invention is placed between the legs of a patient who is lying supine or prone on a radiation therapy support platform. The slide member 40 is manually moved toward the patient's perineum using the handle 50 to move the slide member 40 so that the leading end of the slide member 40 pushes the perineal scar cephalad. When the scar has been pushed to the desired position, the slide member 40 is releasably locked in place to hold the scar in the desired position during subsequent radiation therapy.

Advantageously, a replaceable push pad 44 is attached to the leading end of the slide member 40. Either the leading end of the slide member 40 or the push pad 44 if such a pad is being used engages the area of the patient's scar. The leading end of the slide member 40 or the push pad 44 when present pushes the area of the scar cephalad and defines the position of the scar so that the radiation dose to the skin near the scar (and in particular to the genitalia of the patient) is greatly reduced in comparison to the radiation dose that would be received in the absence of the pushing and positioning of the scar by the device of the present invention. A significant advantage of using a push pad 44 is that the push pad 44 can be made of a relatively soft, resilient material such as foamed styrene, and the push pad 44 can be shaped so that the leading end of the push pad 44 has a contour that matches the contour of the patient's perineum.

In the preferred embodiment as illustrated, the handle 50 extends upwardly from an upper edge of the slide plate 40 to form an elongate hand grasp that is positioned alongside the upper edge of the slide plate 40. The releasable locking member advantageously comprises a spring biased engagement member that makes locking engagement with a corresponding engagement member on at least one of the side plates 42 of the guide and support member 30. The spring biased engagement member preferably has a manually operated release that allows the spring biased engagement member to be manually retracted against the spring bias to release the engagement of the spring biased engagement member to the corresponding engagement member on the side plate of the guide and support member 30.

In the illustrated embodiment, the handle 50 forms an arch that extends upwardly from the upper surface of the slide plate 42 of the slide member 40. Two elongate springs 52 are located in corresponding elongate bores in the opposite ends of the handle 50. The springs 52 exert a downward bias force on a pair of guide rods 54 that are positioned in the elongate bores in the handle 50. The guide rods 54 extend downwardly into notched openings 56 formed between the handle 50 and the upper surface of the slide plate 42 of the slide member 40.

The ends of the guide rods 54 that project into the notched openings 56 are connected to a flat bar 60 that forms a engagement member which extends flatwise adjacent to the upper surface of the slide plate 42. The flat bar 60 has a width that is greater than the thickness of the slide plate 42 so that the opposite sides of the flat bar 60 extend beyond the opposite sides of the slide plate 42. The portions of the opposite sides of the flat bar 60 that extend beyond the opposite sides of the slide plate 42 contact the upper edges of the side plates 32 of the guide and support member 30. The flat bar 60 is forced by the bias of the springs 52 so that the opposite sides of the flat bar 60 make forced contact with a corresponding engagement member formed at or comprising the upper edges of the side plates 32. The engagement between the flat bar 60 and the upper edges of the side plates 32 create the locking mechanism for restraining or locking the slide member 40 to the guide and support member 30.

A releasing mechanism is provided to release the locking of the engagement between the flat bar 60 and the upper edges of the side plates 32. In the illustrated embodiment, the releasing mechanism takes the form of a U-shaped pull member 62 that extends upwardly from the flat bar 60 to lie spaced slightly from the inside surface of the handle 50. The pull member 62 is positioned close enough to the handle 50 and conforms to the inner side of the handle 50 such that when one grasps the handle 50, the pull member 62 is also grasped. The pull member 62 in essence becomes a part of the underside of the handle 50 and is grasped concurrently with the handle 50. When the handle 50 is grasped and then squeezed, the pull member 62 is pulled upwardly and in turn pulls the flat bar 60 upwardly so that the engagement between the flat bar 60 and the upper edges of the side plates 32 is interrupted. When the engagement is interrupted, the slide member 40 can be moved in its sliding motion. When the slide member 40 is moved to its desired position, the handle 50 is released so as to release the pull member 62 and re-establish engagement between the flat bar 60 and the upper edges of the side plates 32 to thereby lock the slide member 40 in its desired position.

The engagement between the flat bar 60 and the upper edges of the side plates 32 can be enhanced by creating high friction surfaces on the mating surfaces of the flat bar 60 and the side plates 32. The frictional engagement surfaces can be knurls or other roughened surface formed integrally on the mating surfaces of the flat bar 60 and the side plates 32. Alternatively, the frictional engagement surfaces can be high frictional surfaces similar to sandpaper formed on the mating surfaces of the flat bar 60 and the side plates 32.

In the embodiment shown in the drawings, a mechanical adjusting means is provided in combination with the releasable locking mechanism for fine adjustment of the position of the slide member 40. In the illustrated embodiment, a engagement member is formed on at least one of the side plates 32 of the guide and support member 30 and comprises an elongate threaded screw 66 that is mounted alongside an upper side of at least one of the side plates 32. The spring biased engagement member, i.e., the flat bar 60, of the releasable locking mechanism has grooves in the surface thereof that mate with and engage the threads of the elongate threaded screw 66 or can otherwise conform to the threads of the elongate threaded screw 66 when the spring biased engagement member, i.e., the flat bar 60, makes engagement with the elongate threaded screw 66.

Means are preferably provided for manually rotating the threaded screw 66 about its longitudinal axis so that when the spring biased engagement member, i.e., the flat bar 60, makes engagement with the elongate threaded screw 66, the elongate threaded screw 66 can be rotated to provide fine adjustment of the position to which the slide member 40 is releasably locked. As illustrated, a crank wheel 70 is connected to the end of the elongate threaded screw 66 and can be used to rotate the elongate threaded screw 66.

Although a preferred embodiment of the device of the present invention has been illustrated and described, it is to be understood that the present disclosure is made by way of example and that various other embodiments are possible without departing from the subject matter coming within the scope of the following claims, which subject matter is regarded as the invention.

We claim:

1. A device for pushing a scar in a perineal region of a patient whose rectum and anus have previously been surgical removed, so that the scar can be optimally positioned during radiation treatment of a rectal area of the patient, said device comprising a base that is positioned beneath a patient's legs as the patient lies supine or prone on a radiation therapy support platform;

a guide and support member extending upwardly from said base so that said guide and support member positioned between thighs of the patient;

a slide member supported by said guide and support member, said slide member being constrained to slide back and forth along the guide and support member in a direction substantially parallel to the patient's legs so that pressure exerted on the patient's perineum by a leading end of the slide member can be adjusted;

means for manually moving the slide member in its movement relative to said guide and support member; and means for retaining said slide member in any selected position along the movement of said slide member relative to said guide and support member, whereby the slide member can be manually moved toward the patient's perineum so that the leading end of the slide member pushes the perineal scar cephalad, and then holds the scar in proper position during subsequent radiation therapy of the rectal area of the patient.

2. A device in accordance with claim 1 wherein said means for manually moving the slide member is a handle that is positioned along the top of said slide member.

3. A device in accordance with claim 2 further including a releasable locking mechanism associated with said slide member, wherein said releasable locking mechanism can be used to releasably lock said slide member in any selected position along the movement of said slide member relative to said guide and support member.

4. A device in accordance with claim 3 wherein a mechanical adjusting means is provided in combination with said releasable locking mechanism for fine adjustment of the position to which said slide member is releasably locked.

5. A device in accordance with claim 3 wherein said releasable locking mechanism can be released by squeezing the handle.

6. A device in accordance with claim 1 wherein a replaceable push pad is attached to the leading end of the slide member so that the push pad engages the area of the patient's scar, wherein said push pad conforms to a contour of the patient's perineum and to push the scar to a position that will reduce a radiation dose to the skin near the scar in comparison to that which would be received in a absence of the scar being pushed and positioned by the push pad.

7. A device in accordance with claim 1 wherein said base is an elongate member that is positioned between the legs of the patient so that a longitudinal axis of said base lies substantially parallel with and between the patient's legs, said base having a substantially flat bottom that lies flatwise on a sheet or other cover covering a support platform, with said base further having two opposite longitudinal top sides that slope inwardly from respective longitudinal side edges of said flat bottom toward a central, vertical plane through the longitudinal axis of said base to form shallow, inwardly slanted top surfaces upon which the patient's legs rest when the patient lies on the support platform, whereby weight of the patient's legs acts on the top sides of said base to hold the base in a firm, stable position on the support platform.

8. A device in accordance with claim 1 wherein said base has attached to its bottom surface at least one unidirectional oriented fiber strip that interdigitates with a weave of a sheet or other cover placed on the support platform, said interdigitation preventing slippage of said base toward the patient's feet but permitting said base to be slid over said sheet or other cover toward the patient's head.

9. A device in accordance with claim 1 wherein said guide and support member comprises a pair of spaced apart, substantially planar side plates that extend substantially vertically upwardly from said base; and said slide member comprises a substantially planar slide plate that is received substantially vertically between said pair of side plates so that a lower edge of said slide plate slides back and forth along said base while opposite, broad sides of said slide plate are supported by said side plates and guided in back and forth movement between and along said side plates.

10. A device in accordance with claim 9 wherein a handle extends upwardly from a top of said slide plate to form an elongate hand grasp that is positioned alongside the top of said slide plate.

11. A device in accordance with claim 10 wherein a releasable locking mechanism is associated with said slide member with said releasable locking mechanism being adapted to releasably lock said slide member in any selected position along the movement of said slide member relative to said guide and support member; and said releasable locking member comprises a spring biased engagement member that makes locking engagement with a corresponding engagement member on at least one of the side plates of said guide and support member, said spring biased engagement member having a manually operated release that allows the spring biased engagement member to be manually retracted against the spring bias to release the engagement of the spring biased engagement member to the corresponding engagement member on the side plate of said guide and support member.

12. A device in accordance with claim 11 wherein the corresponding engagement member on one of the side plates of said guide and support member comprises an elongate threaded screw that is mounted alongside an upper side of said one of the side plates;

the spring biased engagement member of said releasable locking member mates with and engages the threads of said elongate threaded screw when the spring biased engagement member makes engagement with said elongate threaded screw; and means are provided for manually rotating said threaded screw about its longitudinal axis so that when the spring biased engagement member of said releasable locking member makes engagement with said elongate threaded screw, the elongate threaded screw can be rotated to provide fine adjustment of the position to which said slide member is releasably locked.

* * * * *